(12) United States Patent
Scholtz

(10) Patent No.: US 9,423,548 B2
(45) Date of Patent: Aug. 23, 2016

(54) MULTIPLE WAVELENGTH LIGHT SOURCE AND SIGNAL COLLECTION DEVICE AND METHODS FOR USING THE SAME

(75) Inventor: James I. Scholtz, New York, NY (US)

(73) Assignee: The Research Foundation of the City University of New York, New York, NY (US)

( * ) Notice: Subject to any disclaimer, the term of this patent is extended or adjusted under 35 U.S.C. 154(b) by 234 days.

(21) Appl. No.: 14/004,565

(22) PCT Filed: May 4, 2012

(86) PCT No.: PCT/US2012/036531
§ 371 (c)(1),
(2), (4) Date: Jan. 30, 2014

(87) PCT Pub. No.: WO2012/151492
PCT Pub. Date: Nov. 8, 2012

(65) Prior Publication Data
US 2014/0140087 A1    May 22, 2014

Related U.S. Application Data

(60) Provisional application No. 61/482,526, filed on May 4, 2011.

(51) Int. Cl.
*F21V 8/00* (2006.01)
*G02B 6/32* (2006.01)
(Continued)

(52) U.S. Cl.
CPC ............ *G02B 6/0005* (2013.01); *G01N 21/474* (2013.01); *G02B 6/32* (2013.01); *G02B 6/4204* (2013.01); *G01N 2021/4747* (2013.01); *G02B 6/4249* (2013.01)

(58) Field of Classification Search
CPC ...... G02B 6/0005; G02B 6/32; G02B 6/4204; G02B 6/4249
See application file for complete search history.

(56) References Cited

U.S. PATENT DOCUMENTS 4,763,975 A * 8/1988 Scifres ................. G02B 6/2552
385/115
4,881,215 A * 11/1989 Horie ................... G11B 7/0033
235/454

(Continued)

FOREIGN PATENT DOCUMENTS

JP    05022530 A  *  1/1993
JP    10200483 A  *  7/1998
(Continued)

OTHER PUBLICATIONS

International Search Report and Written Opinion dated Nov. 16, 2012 for PCT/US12/36531.
(Continued)

*Primary Examiner* — Peter Radkowski
(74) *Attorney, Agent, or Firm* — Burns & Levinson LLP; Orlando Lopez

(57) ABSTRACT

An optical device including a first optical fiber providing optical communication between one surface of the device and a target, the first optical fiber having one end located at that one surface of the device, a number of semiconductor light sources, each semiconductor light source from the number of semiconductor light sources disposed on a surface surrounding the first optical fiber and located away from the one end, and an optical system optically disposed to receive electromagnetic radiation from each semiconductor light source and image the electromagnetic radiation received from each semiconductor light source onto a core area of the one end of the first optical fiber.

24 Claims, 10 Drawing Sheets

(51) Int. Cl.
*G02B 6/42* (2006.01)
*G01N 21/47* (2006.01)

(56) References Cited

U.S. PATENT DOCUMENTS

| | | | | |
|---|---|---|---|---|
| 4,988,154 A * | 1/1991 | Hansen | ............... | G03H 1/0406 359/22 |
| 5,228,103 A * | 7/1993 | Chen | ............... | G01J 3/0259 359/333 |
| 5,258,989 A * | 11/1993 | Raven | ............... | A61B 18/245 359/669 |
| 5,278,687 A * | 1/1994 | Jannson | ............... | H04J 14/02 398/79 |
| 5,369,661 A * | 11/1994 | Yamaguchi | ............... | G02B 3/0087 372/101 |
| 5,526,155 A * | 6/1996 | Knox | ............... | G02B 6/2931 370/480 |
| 6,275,317 B1 * | 8/2001 | Doerr | ............... | H04B 10/505 398/183 |
| 6,910,780 B2 * | 6/2005 | Vail | ............... | H01S 5/40 359/577 |
| 6,999,400 B1 * | 2/2006 | Nakano | ............... | G01M 11/0221 359/719 |
| 7,148,963 B2 | 12/2006 | Owen et al. | | |
| 7,209,287 B2 * | 4/2007 | Lauer | ............... | G02B 21/004 250/458.1 |
| 7,312,432 B2 * | 12/2007 | Liang | ............... | G02B 21/06 250/216 |
| 7,315,372 B1 * | 1/2008 | Billard | ............... | G01N 15/1434 356/338 |
| 7,336,351 B1 | 2/2008 | Sweet et al. | | |
| 2002/0076480 A1 * | 6/2002 | Hsieh | ............... | G02B 6/4246 427/8 |
| 2003/0036356 A1 * | 2/2003 | Witehira | ............... | H04B 10/11 455/41.1 |
| 2003/0170028 A1 * | 9/2003 | Mori | ............... | H04B 10/2537 398/79 |
| 2004/0004176 A1 * | 1/2004 | Liang | ............... | G02B 21/06 250/208.1 |
| 2004/0013431 A1 * | 1/2004 | Vail | ............... | H01S 5/40 398/84 |
| 2004/0032650 A1 * | 2/2004 | Lauer | ............... | G02B 21/004 359/385 |
| 2004/0141684 A1 * | 7/2004 | Wildnauer | ............... | G02B 6/29307 385/24 |
| 2007/0031086 A1 * | 2/2007 | Wildnauer | ............... | G02B 6/29307 385/47 |
| 2007/0127020 A1 | 6/2007 | Hikichi et al. | | |
| 2008/0018893 A1 * | 1/2008 | Billard | ............... | G01N 21/532 356/338 |
| 2008/0073486 A1 * | 3/2008 | Liang | ............... | G02B 21/06 250/206 |
| 2010/0294948 A1 | 11/2010 | Fukuzawa | | |

FOREIGN PATENT DOCUMENTS

| | | | |
|---|---|---|---|
| JP | 2001272623 A | * | 10/2001 |
| JP | 3269980 B2 | * | 4/2002 |
| WO | 9316406 A1 | | 8/1993 |

OTHER PUBLICATIONS

Dietz, P. et al. Very Low-Cost Sensing and Communication Using Bidirectional LEDs. ACM International Conference on Ubiquitous Computing (UbiComp), Oct. 2003: 1-19.

* cited by examiner

MULTIPLE WAVELENGTH LIGHT SOURCE AND SIGNAL COLLECTION DEVICE AND METHODS FOR USING THE SAME

CROSS-REFERENCE TO RELATED APPLICATIONS

This application is a U.S. national stage application under 35 U.S.C. 371 of co-pending International Application No. PCT/US12/36531 filed on May 4, 2012 and entitled MULTIPLE WAVELENGTH LIGHT SOURCE AND SIGNAL COLLECTION DEVICE AND METHODS FOR USING THE SAME, which in turn claims priority to U.S. Provisional Patent Application No. 61/482,526 filed on May 4, 2011, which is incorporated by reference herein in its entirety for all purposes.

BACKGROUND

The disclosed subject matter relates to light source and signal collection device and methods for using the same.

Conventional optical fiber bundles are composed of multiple small core fibers that are bunched together into a single cable. Multiple light sources, such as a light emitting diodes (LEDs), are also used with these optical fiber bundles, where each light source is aligned with one of the small core fibers. In addition, a separate fiber within the optical fiber bundle is typically used to collect fluorescence emission for analysis.

Many approaches attempt to solve this issue of coupling each light source to a fiber by using dichroic mirrors to couple multiple LEDs to a single fiber. However, these mirrors and other optical components needed to create these optical structures are expensive, require sufficiently separated wavelengths, and are not scalable. In addition to these optical components, note that the optical fiber bundles themselves are also expensive. For example, a typical optical fiber bundle for use in these optical structures can cost in the range of $1,000 through $3,000 depending on the number of fibers needed. It should also be noted that this is not practical for wavelength scaling as the outer diameter of the fiber bundle becomes significantly large. Further, each individual fiber has a small diameter, which reduces the amount of light that can be coupled and the amount of emission that can be collected.

Accordingly, devices and methods are provided that overcome these and other deficiencies of the prior art.

SUMMARY

In accordance with various embodiments of the disclosed subject matter, devices and methods are provided that overcome the above described and other deficiencies of the prior art are disclosed hereinbelow.

In one or more embodiments, the optical device of these teachings includes a first optical fiber providing optical communication between one surface of the device and a target, the first optical fiber having one end located at that one surface of the device, a number of semiconductor light sources, each semiconductor light source from the number of semiconductor light sources disposed on a surface surrounding the first optical fiber and located away from the one end, and an optical system optically disposed to receive electromagnetic radiation from each semiconductor light source and image the electromagnetic radiation received from each semiconductor light source onto a core area of the one end of the first optical fiber.

In some embodiments, the optical device is further configured to transmit the emitted light through the single fiber waveguide (also referred to as a second optical fiber) for analysis using an analysis component.

In some embodiments, each of the number of semiconductor light sources are mounted within lens tubes. In one or more embodiments, the optical system includes a number of lenses, each one lens from the number of lenses disposed away and receiving electromagnetic radiation from one semiconductor light source from the number of semiconductor light sources, each one lens being mounted within one of the lens tubes, constituting a number of lens tube subsystems.

In some embodiments, each lens tube subsystem is located substantially parallel to an optical axis defined by a line perpendicular to the core area of the first optical fiber, each lens tube subsystem being located at a radial distance away from the optical axis defined by the line perpendicular to the core area of the first optical fiber, the radial distance being larger than a radius of the first optical fiber, each lens tube subsystem being disposed to distance away from the one surface, and the optical system also includes an optical subsystem optically disposed to receive electromagnetic radiation from each lens tube subsystem and image the electromagnetic radiation received from each lens tube subsystem onto a core area of the one end of the first optical fiber.

In some embodiments, the optical subsystem includes a first lens disposed between the number of lens tube subsystems and the one surface of the device, the first lens having a number of openings, each opening from the number of openings being optically disposed to receive the electromagnetic radiation from one lens tube subsystem, and a second lens disposed between the first lens and the one surface of the device, the second lens being optically disposed to receive electromagnetic radiation from each opening from the number of openings and image the electromagnetic radiation received from each opening onto a core area of the one end of the first optical fiber.

In some other embodiments, the optical subsystem includes a first lens disposed between the number of lens tube subsystems and the one surface, the first lens being optically disposed to receive the electromagnetic radiation from each lens tube subsystem and image the electromagnetic radiation received from each lens tube subsystem onto a core area of the one end of the first optical fiber, and a second lens disposed between the first lens and the one surface and adjacent to the first lens, the second lens having an optical axis substantially collinear with an optical axis of the first lens and having an area smaller than an area of the first lens, the second lens being optically disposed to image electromagnetic radiation emanating from the one end of the first optical fiber onto a core area of the second optical fiber end.

A number of other device embodiments are also disclosed herein below.

One or more embodiments of methods of using the device of these teachings are also disclosed.

For a better understanding of the present teachings, together with other and further objects thereof, reference is made to the accompanying drawings and detailed description and its scope will be pointed out in the appended claims.

DETAILED DESCRIPTION

Figure 1:
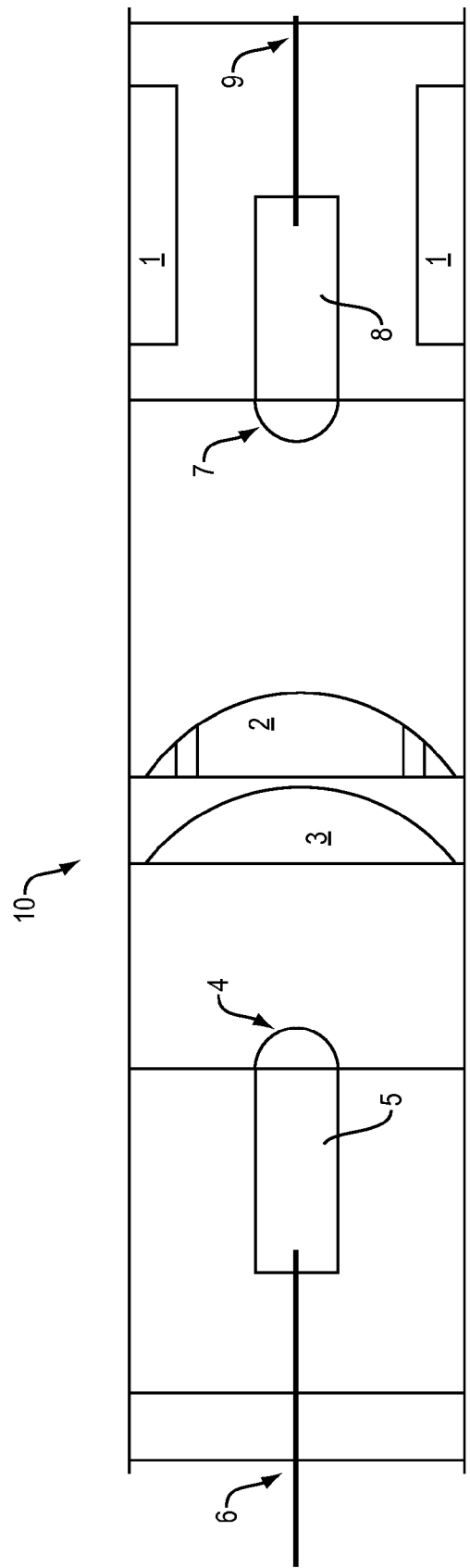
FIG. 1 shows a schematic representation of one embodiment of the system of these teachings.

The following detailed description is of the best currently contemplated modes of carrying out these teachings. The description is not to be taken in a limiting sense, but is made merely for the purpose of illustrating the general principles of these teachings, since the scope of these teachings is best defined by the appended claims.

The present teachings will be more completely understood through the following description, which should be read in conjunction with the drawings. In this description, like numbers refer to similar elements within various embodiments of the present disclosure. Within this description, the claims will be explained with respect to embodiments. The skilled artisan will readily appreciate that the methods, apparatus and systems described herein are merely exemplary and that variations can be made without departing from the spirit and scope of the disclosure.

As used herein, the singular forms "a," "an," and "the" include the plural reference unless the context clearly dictates otherwise.

Except where otherwise indicated, all numbers expressing quantities of ingredients, dimensions, and so forth used in the specification and claims are to be understood as being modified in all instances by the term "about."

Generally speaking, mechanisms are provided for coupling multiple semiconductor light sources to a single optical fiber waveguide to allow illumination of a remote target sample. In addition, the single optical fiber waveguide can be configured to collect light incident upon a target sample that scatters, reflects, and/or emits fluorescence and to transmit the collected scatter, reflection, and/or fluorescence emission to an analysis component. Embodiments in which the analysis component is attached or integrated are within the scope of these teachings.

"Light," as used herein, refers to electromagnetic radiation and does not limit the wavelength or spectrum of the electromagnetic radiation.

"Optical fiber," as used herein, refers to both optical fibers and optical waveguides.

As used herein, a light source can be any suitable light source, such as, a light emitting diode (LED), a gallium nitride laser, a Fabry-Perot laser, a quantum cascade laser that emits mid-infrared light or far-infrared light, a vertical cavity surface emitting laser (VCSEL), a superluminescent LED (SLED), or any other suitable semiconductor light source.

As used herein, a lens tube can be any component on which the semiconductor light source and \other optical components can be mounted.

As used herein, a surface refers to a locus of points whether or not a physical structure also resides at that locus of points.

It should be noted that, in using one or more of these light sources, the wavelength capability of the device, with continuous range in select regions, can be, in one embodiment, between about 270 nanometers through about 4600 nanometers. It should further be noted that particular light sources can be used to obtain particular wavelength ranges.

The device can be used in a variety of applications. For example, the device can provide a low-cost, robust, wavelength scalable light source while also providing sample collection of light for analysis using a single optical fiber. In addition, the device can dramatically increase remote sensing signal strength as compared with commercially available designs or structures.

In one or more embodiments, the optical device of these teachings includes a first optical fiber providing optical communication between one surface of the device and a target, the first optical fiber having one end located at that one surface of the device, a number of semiconductor light sources, each semiconductor light source from the number of semiconductor light sources disposed on a surface surrounding the first optical fiber and located away from the one end, and an optical system optically disposed to receive electromagnetic radiation from each semiconductor light source and image the electromagnetic radiation received from each semiconductor light source onto a core area of the one end of the first optical fiber.

In one instance, at least some semiconductor light sources from the number of semiconductor light sources emit electromagnetic radiation at a wavelength different from a wavelength of electromagnetic radiation emitted by other semiconductor light sources from the number of semiconductor light sources.

In one or more embodiments, the optical device of these teachings also includes a second optical fiber providing optical communication between another surface of the device and an analysis component, the second optical fiber having a second optical fiber end located at the other surface of the apparatus; the other surface being disposed away from and facing the one surface, the optical system also being optically disposed to image electromagnetic radiation emanating from the one end of the first optical fiber onto a core area of the second optical fiber end.

In one or more embodiments, the optical system includes a number of lenses; each one lens from the number of lenses disposed away and receiving electromagnetic radiation from one semiconductor light source from the number of semiconductor light sources; the one lens and the one semiconductor light source constituting a lens/semiconductor light source combination and being one of a number of lens/semiconductor light source combinations; each lens/semiconductor light source combination being located in a lens tube, constituting one of a number of lens tube subsystems.

In one instance of the one or more embodiments of devices of these teachings including a number of lens tube subsystems, each lens tube subsystem is located at an angle with respect to an optical axis defined by a line perpendicular to the core area of the first optical fiber; each lens tube optical axis intersecting the core area of the first optical fiber.

In another instance of the one or more embodiments of the device of these teachings include a number of lens tube subsystems, each lens tube subsystem is located substantially parallel to an optical axis defined by a line perpendicular to the core area of the first optical fiber, each lens tube subsystem being located at a radial distance away from the optical axis defined by the line perpendicular to the core area of the first optical fiber, the radial distance being larger than a radius of the first optical fiber, each lens tube subsystem being disposed a distance away from the one surface, and the optical system also comprises an optical subsystem optically disposed to receive electromagnetic radiation from each lens tube subsystem and image the electromagnetic radiation received from each lens tube subsystem onto a core area of the one end. In another instance in which the one or more embodiments include a first optical fiber providing optical communication between one surface of the device and a target, the optical subsystem includes a first lens disposed between the number of lens tube subsystems and the one surface, the first lens being optically disposed to receive the electromagnetic radiation from each lens tube subsystem and image the electromagnetic radiation received from each lens tube subsystem onto a core area of the one end, and a second lens disposed between the first lens and the one surface and adjacent to the first lens, the second lens having an optical axis substantially collinear with an optical axis of the first lens and having an area smaller than an area of the first lens, the second lens being optically disposed to image electromagnetic radiation emanating from the one end of the first optical fiber onto a core area of second optical fiber end.

In another instance in which of the one or more embodiments of the device of these teachings include a number of lens tube subsystems, each lens tube subsystem being located substantially parallel to an optical axis defined by a line perpendicular to the core area of the first optical fiber, at least one semiconductor light source is located substantially radially opposite to another semiconductor light source, the other semiconductor light source being operated as a detector; the other semiconductor light source detecting an output of the one or more semiconductor light sources. The operation of the semiconductor light source as a detector could be, for example, as described in Paul Dietz, William Yerazunis, Darren Leigh, Very Low-Cost Sensing and Communication Using Bidirectional LEDs, MITSUBISHI ELECTRIC RESEARCH LABORATORIES, TR2003-35, July 2003, incorporated by reference herein in its entirety and for all purposes.

In yet another embodiment, one or more neutral density filters are optically disposed to reduce optical noise by reducing the amount of stray light in the device. In one exemplary embodiment, two "aperture" stops are included in the device to increase the S/N ratio. The first is donut shaped, fabricated from a neutral density (ND) filter, and placed midway between the Front Lens and the first optical fiber. In this location, the ND filter has an opportunity to extinguish scatter in both directions. The other configuration is an ND filter around the first optical fiber in which the ND filter has a through hole in the center. The ND filter is positioned against the wall/fiber mount. Both of these significantly reduce the amount of stray light in the device.

In order to better elucidate the present teachings, a number of exemplary embodiments are presented below. It should be noted that these teachings are not limited to only those exemplary embodiments.

Figure 2:
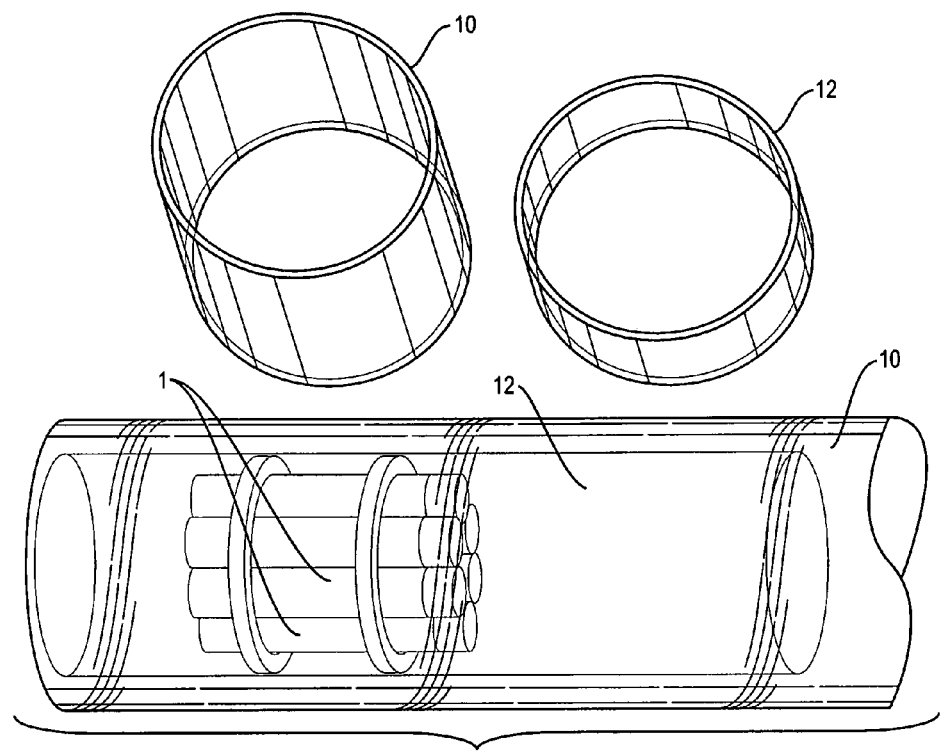
FIG. 2 shows a graphical view of a portion of one embodiment of the system of these teachings.

FIG. 1 shows a top down view of an illustrative device in accordance with some embodiments of the disclosed subject matter. As shown, the device can include a lens tube assembly 1. The lens tube assembly 1 and other components of the device are placed within a support tube 10. As shown in FIG. 2, support tube 10 can be fabricated such that the lens tube assembly 1 and other components are compressed and sealed within the support tube 10, thereby providing a robust mechanical design.

In some embodiments, the device can include spacer tubes 12 such as the one shown in FIG. 2. As the components of the device are placed within support tube 10, the distances between individual components can be maintained using the spacer tubes 12.

Although FIGS. 1 and 2 illustrate that the lens tube assembly, the support tube, and other components of the device are constructed as cylinders having a given dimension or as structures accommodating those cylinders, this is merely illustrative. Generally speaking, the lens tube assembly, the support tube, and other components of the device can be constructed in any other suitable approach such that multiple semiconductor light sources can be coupled to a single optical fiber waveguide. In some embodiments, the lens tube assembly, the support tube, spacer tubes, and the other components of the device are constructed to substantially reduce the degrees of freedom in the alignment of the optical components, thus reducing alignment time and complexity.

It should also be noted that, for continuous power transfer applications with a high density of LED elements, heat sinking, and thermal dissipation may be considered when fabricating the components of the device. For example, LEDs generally have a 6% electricity to light conversion efficiency. With such a design, the mounting plates, lens tubes, and/or support tube can be constructed using copper, aluminum, and/or any other suitable material. In addition, these components for supporting and/or accommodating the semiconductor light sources can be passively or actively cooled using, for example, heat sinks.

Figure 3:
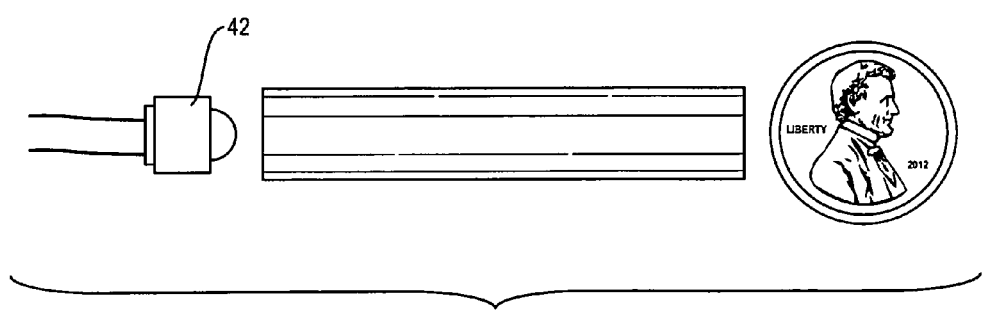
FIG. 3 shows a graphical view of the component of one embodiment of the system of these teachings.

Referring back to the lens tube assembly 1 of FIG. 1, the lens tube assembly 1 allows multiple semiconductor light sources to be coupled to a single optical fiber waveguide. A semiconductor light source can be secured within a lens tube, where a lens is placed at the other end of the lens tube. In one instance, not a limitation of these teachings, the lens is a collimating lens. This is shown in further detail in FIG. 3. As shown, a lens tube has been fabricated that accommodates a mounted LED 42 on one end of the lens tube and a collimation lens (represented by the object) at the other end of the lens tube. (Although an LED is used in the exemplary embodiment, it should be noted that these teachings are not limited only to LEDs.)

It should be noted that, in some embodiments, collimation may not provide optimal results due to the nature of LEDs. Any suitable optics can be selected for use with the semiconductor light source. For example, optical components can be selected that, when combined with front lens 3, provide the highest intensity light to be incident upon the entrance face of power transfer optical fiber 6. In another example, band pass filters can be positioned in the tubes to allow an even narrower bandwidth.

Figure 1A:
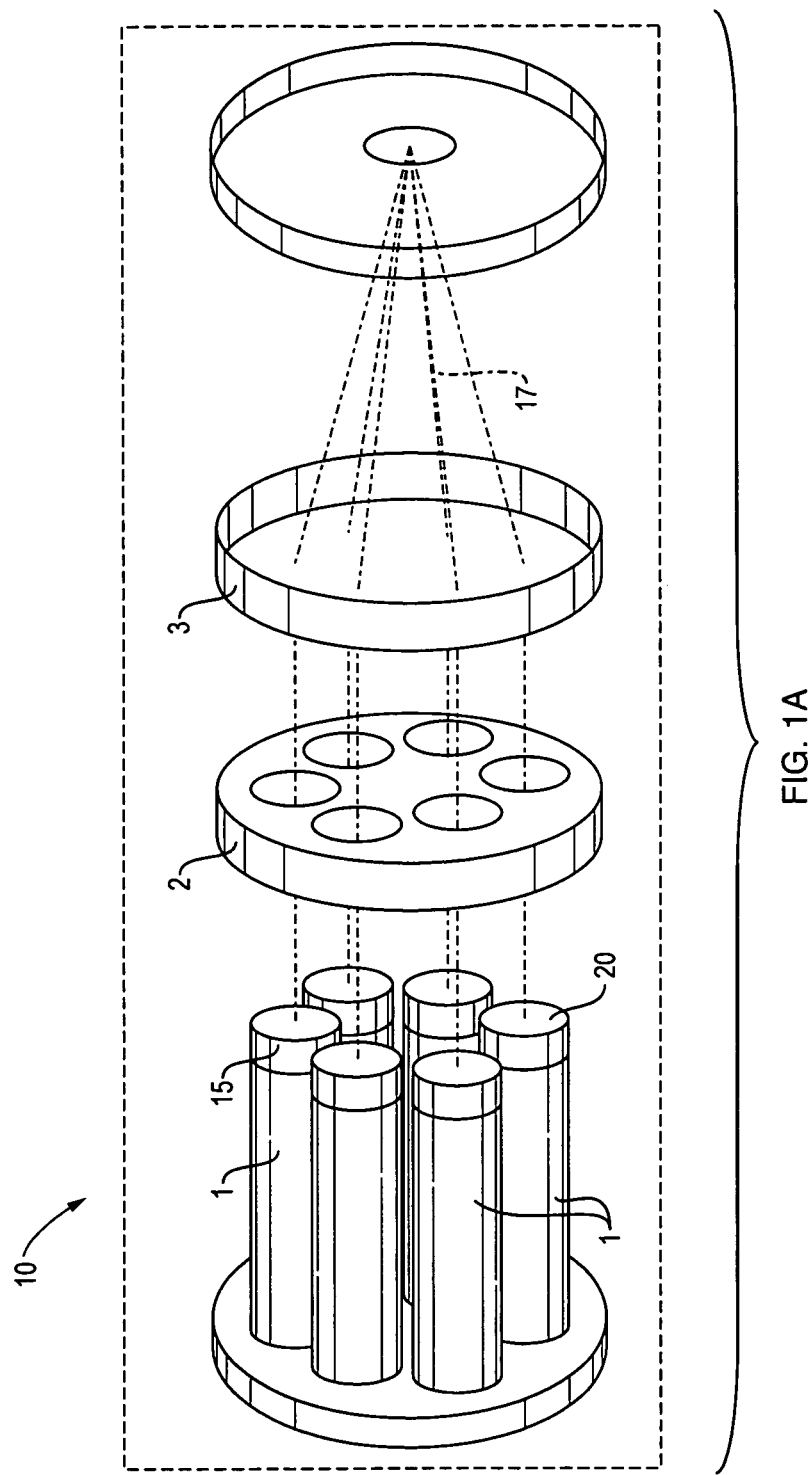
FIG. 1a shows a perspective view of one embodiment of the system of this teaching.

FIG. 1a shows an embodiment in which a number of lens tube subsystems, each lens tube subsystem being located substantially parallel to an optical axis defined by a line perpendicular to the core area of the first optical fiber, at least one semiconductor light source is located substantially radially opposite to another semiconductor light source, the other semiconductor light source being operated as a detector; the other semiconductor light source detecting an output of the one or more semiconductor light sources. Referring to FIG. 1a, in the embodiment shown therein, lens tube subsystems 1, 15, 20, each including one semiconductor light source and, in some embodiments, optical components, are located substantially parallel to an optical axis 17. One semiconductor light source and light tube 15 is located substantially radially opposite to another semiconductor light source and light tube 20. In the embodiment shown in FIG. 1*a*, the semiconductor light source in light tube 20 is operated as a detector, detecting an output of the semiconductor light source in the light tube 15 that is radially opposite. Other components are used and labeled as in FIG. 1.

Figure 1B:
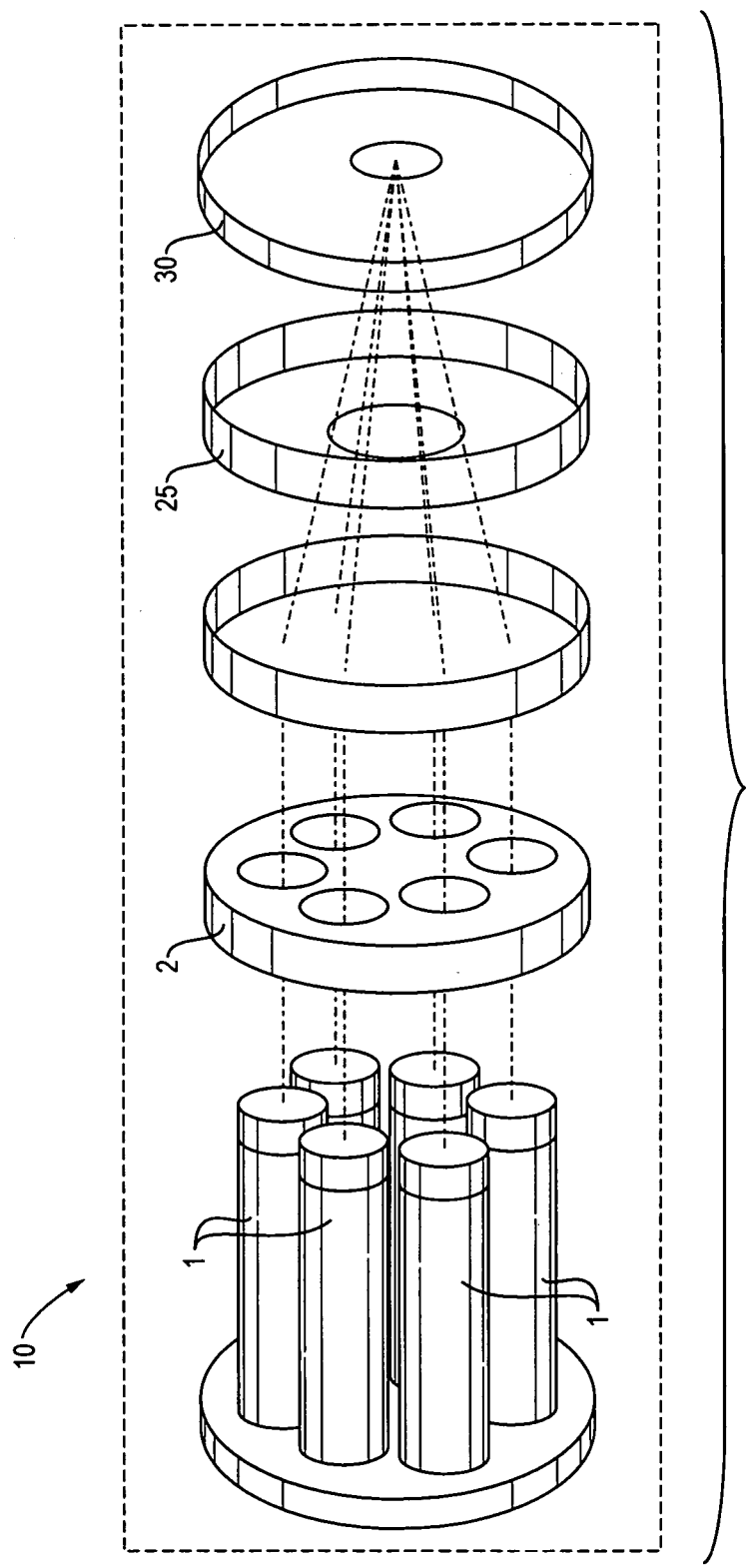
FIG. 1b shows a perspective view of another embodiment of the system of these teachings.

FIG. 1*b* shows an embodiment in which one or more neutral density filters are optically disposed to reduce optical noise by reducing the amount of stray light in the device. Referring to FIG. 1*b*, in the embodiment shown therein, two "aperture" stops 25, 30 are included in the device to increase the S/N ratio. The first 25 is donut shaped, fabricated from a neutral density (ND) filter, and placed midway between the Front Lens and the first optical fiber. In this location, the ND filter 25 has an opportunity to extinguish scatter in both directions. The other configuration is a second ND filter 30 around the first optical fiber in which the ND filter has a through hole in the center. The second ND filter 30 is positioned against the wall/fiber mount. Both of the ND filters significantly reduce the amount of stray light in the device. Other components are used and labeled as in FIG. 1.

Figure 4A:
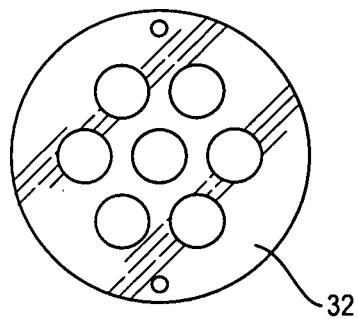
FIGS. 4a-4c and FIG. 5 show a schematic representation and graphical views of components in one embodiment of the system of these teachings.
Figure 4B:
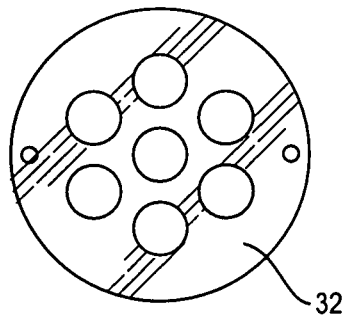
Figure 4C:
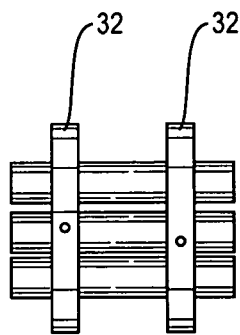

Each of these lens tubes within lens tube assembly 1 is supported by a lens tube support disk 32. An illustrative example of the lens tube support disk 32 in accordance with some embodiments of the disclosed subject matter is shown in FIGS. 4A-4C. As shown, the lens tube support disk 32 secures each of the lens tubes (e.g., the seven lens tubes shown in FIGS. 4A and 4B) and directs the light from multiple LED lens tubes along the longitudinal axis of the support tube (support tube 10 of FIG. 1).

It should be noted that, although FIGS. 4A and 4B illustrates that the lens tube support disk 32 accommodates seven lens tubes, the lens tube support disk 32 can be created that accommodates any suitable number of lens tubes. The device can be scaled to include numerous LED lens tubes by, for example, increasing the diameter of the support tube 10 and other components of the device.

Figure 5:
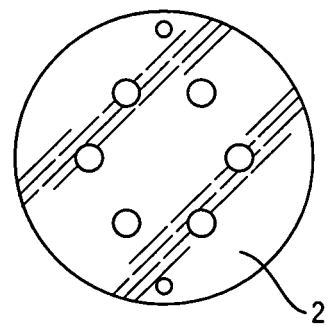
Figure 6:
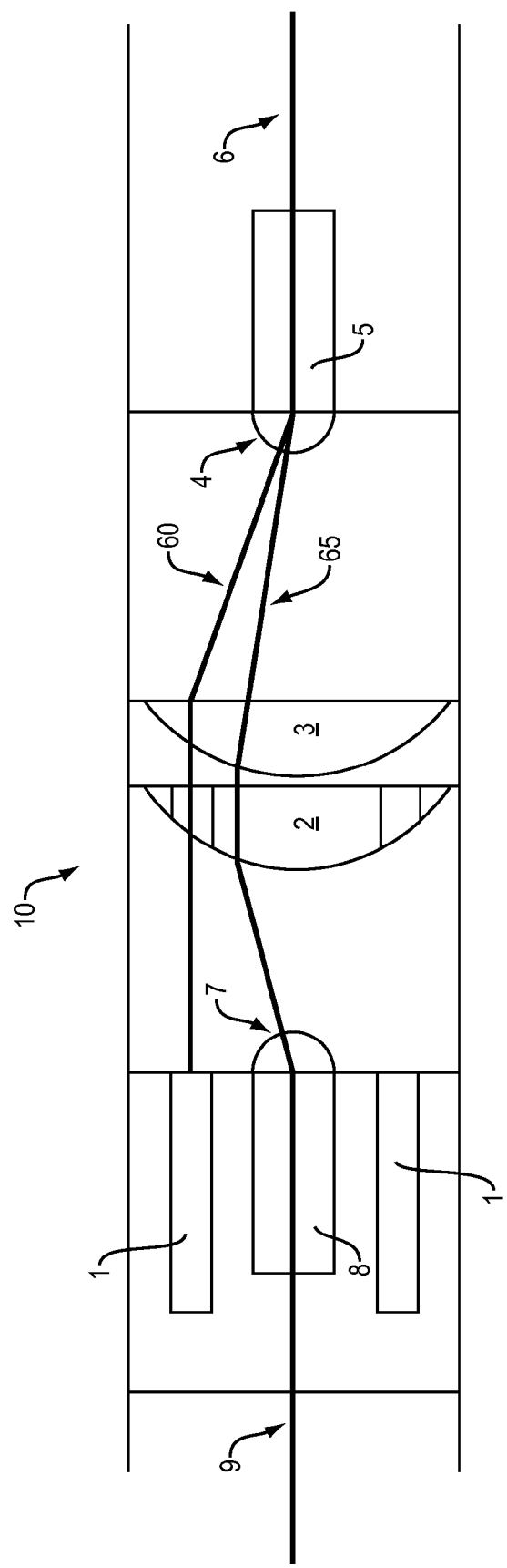
FIG. 6 shows a schematic representation of one embodiment of the system of these teachings.
Figure 7A:
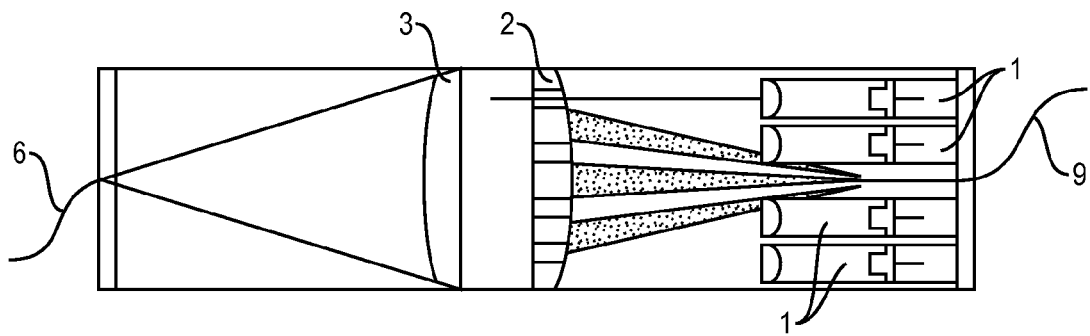
FIGS. 7a-7d show schematic representations of views of another embodiment of the system of these teachings.
Figure 7B:
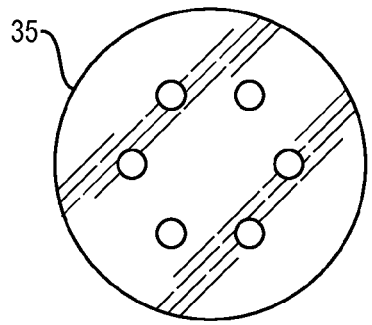
Figure 7C:
Figure 7D:
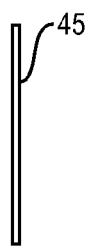

Referring back to FIG. 1, two convergent lenses having a diameter equal to the interior diameter of support tube 10 are positioned within the support tube and in front of the light from the semiconductor light sources. The device includes a first lens 2, which is sometimes referred to herein as the "back lens," that has through holes that match the position of the collimated light paths. An illustrative example of a back lens with through holes is shown in FIG. 5. Note that the light passes through the through holes of the back lens and the lens has no optical effect on the incident light. The light from each of the lens tubes continues to the second convergent lens, which is sometimes referred to herein as the "front lens." The light is refracted at the lens surface and focused to the focal point of the lens on the optical axis. An illustrative diagram of this optical path 60 is shown in FIG. 6. At a location near, but prior to the focal point of the front lens 3, an additional convergent lens 4, sometimes referred to herein as the "first focal lens," is provided, which focuses the light to a focal plane of the lens device.

As used herein, a convergent lens can include, for example, a plano- or bi-convex spherical lens, an aspheric lens, an achromatic lens, an aspheric-achromatic lens, a positive meniscus lens, or any other suitable convergent lens. Alternatively or additionally, a Fresnel lens can be used.

As also used herein, a divergent lens can include, for example a plano- or biconcave spherical lens, an aspheric lens, an achromatic lens, an aspheric-achromatic lens, a positive meniscus lens, or any other suitable divergent lens. Alternatively or additionally, a Fresnel lens can be used.

Referring back to FIG. 1, in some embodiments, the optical system 5 images the multiple light sources with reduced magnification. For coherent, directional light sources of small spot size, first focus lens 4 strongly focuses the light to a tight spot size of numerical aperture (NA) matched to the power optical fiber 6, which can be positioned at the combined focal point of the two lenses. For incoherent, pseudo directional light sources, additional imaging techniques can be used to reduce the spot size for efficient coupling to power optical fiber 6.

It should be noted that, for this device using a single optical fiber (e.g., power optical fiber 6), the individual core has the same diameter as that of a fiber bundle, thereby allowing significant increases in light coupling efficiency. For example, a 600 micron core fiber has a 900% higher entrance face surface area than a 200 micron core. Each LED lens tube light source benefits from this increase in area by increased coupling efficiency and reduced alignment and focusing tolerances, while maintaining an equivalent or smaller diameter cable.

With respect to emission collection, the coupled light from the semiconductor light source travels along the fiber optical waveguide to the opposite end, where it leaves the fiber optical waveguide (e.g., fiber 6) and impacts the intended target. The light exits the fiber optical waveguide as a ring expanding at a rate proportional to the input angle. In some embodiments, optical approaches, such as chemically etched axicons, being either negative or positive, or lenses, being either convex or concave on the tip of the fiber can be used for beam shaping. Individual optical components of these types can also be placed in front of the fiber tip if space allows. The light is reflected, absorbed, and transmitted through the target material and, with the appropriate wavelengths, fluorescence takes place.

At least a portion of the fluorescence emission travels back to the fiber optical waveguide exit face and is coupled, traveling in reverse direction to that of the LED light along the same fiber. This emission light exits the fiber optical waveguide, uniformly filling the entire field of angular width equal to the numerical aperture of the fiber. As shown by path 65 in FIG. 6, the emission light travels back along the same optical path as the LED light, passing through the additional imaging optics 5, first focus lens 4, and front lens 3. At this point, the emission light is collimated. The LED light, in narrow beams, passed through the back lens 2 through holes experiencing no optical effect. The emission fills the entire back lens clear aperture, and thus the light is focused by the back lens 2. The collection loss associated with this lens is equivalent to about the area of the through hole, multiplied by the number of through holes, and divided by the area of the back lens. For example, using the back lens 2 shown in FIG. 5, the collection loss is about 10%. The emission light is focused to a point on the optical axis. At a location near, but prior to the focal point of the back lens, an additional convergent lens 7, sometimes referred to herein as the "second focus lens," is provided. Second focus lens 7 strongly focuses the light to a tight spot size matched to the numerical aperture of analysis optical fiber 9 (the same optical fiber), which is positioned at the combined focal point of these two lenses.

In some embodiments, additional imaging optics 8 can be provided within the device for spot size reduction. As used herein, "imaging optics" can be any suitable optical components for use with the device. For example, in one embodiment, the imaging optics 8 can include one or more convergent lenses, one or more divergent lenses, and any suitable combination thereof. In another example, the imaging optics 8 can include a non-imaging component, such as a tapered conical waveguide or an axicon.

Referring back to FIG. 1, analysis optical fiber 9 transmits the emission light to an attached analysis component. The attached analysis component can be any suitable component, such as a spectrometer, a photomultiplier tube, a charge-coupled device (CCD) camera, a photodiode, or any other suitable device for analysis of optical signals.

In some embodiments, the device can be constructed using alternative designs.

For example, as shown in FIGS. 7-10, alternative designs for the device shown in FIG. 1 are provided.

FIG. 7 illustrates a device with a through hole structure that has three-dimensional symmetry about the horizontal axis, thereby allowing multiple LED lens tubes. As shown, LED lens tubes 1 are positioned for providing multiple wavelengths of light from different LEDs, which are combined for transmission to a fiber 6 and emission on a target source. The lenses can be, for example, a spherical lens, a Fresnel lens, or any other suitable lenses. Using the same fiber 6 and traversing along an optical path through the same lenses 3, 2 and other optical components, emitted light that is collected from the target source is transmitted through the device, by means of an analysis fiber 9, to an attached or integrated analysis device (e.g., a spectrometer). FIG. 7b shows a front end view 35 of the back lens 2. FIG. 7c shows a side view 40 of the back lens in the embodiment in which the back lens is a spherical lens. FIG. 7d shows a side view of the back lens in the embodiment in which the back lens is a Fresnel lens.

Figure 8:
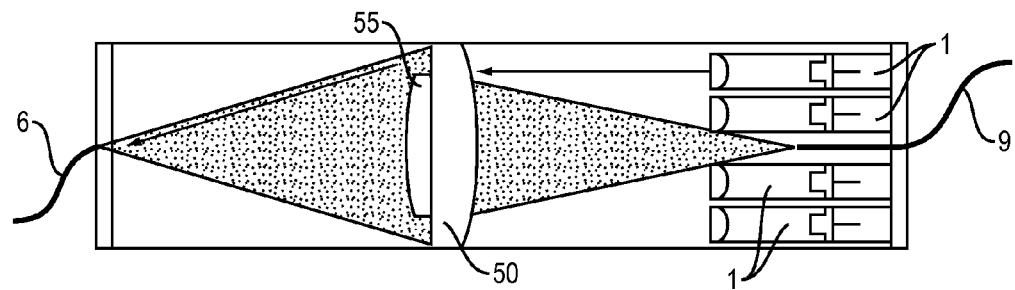
FIG. 8 shows a schematic representation of yet another embodiment of the system of these teachings.

FIG. 8 illustrates an embodiment of the device of these teachings with lenses of different sizes—e.g., a smaller front lens 55 and a larger back lens 15. Even with lenses of different sizes, the device has three-dimensional symmetry about the horizontal axis, thereby allowing multiple LED lens tubes.

Figure 9:
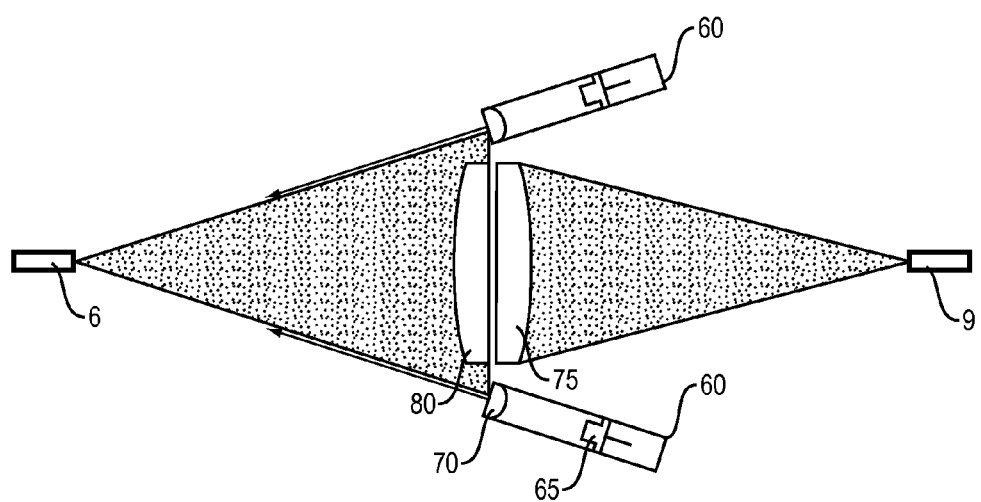
FIG. 9 shows a schematic representation of a further embodiment of the system of these teachings.

FIG. 9 illustrates an embodiment of the device of these teachings with an angled lens tube assembly or structure. As shown, LEDs 65 are mounted in individual lens tubes 60 with each lens tube 60 provided at a given angle. Each lens tube 60 has a lens 70 that focuses the emission on to a core area of the power fiber 6. The front lens 80 and the back lens 75 received the light emitted by power fiber 6 and focus it on to the analysis fiber 9. The angled structure has three-dimensional symmetry about the horizontal axis.

Figure 10A:
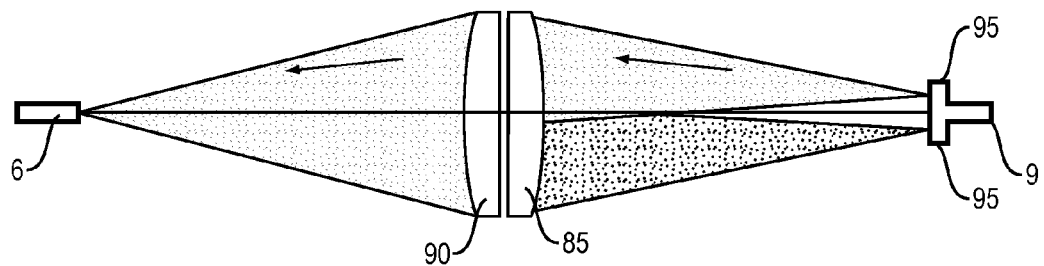
FIGS. 10a-10b show schematic representations of still a further embodiment of the system of these teachings.
Figure 10B:
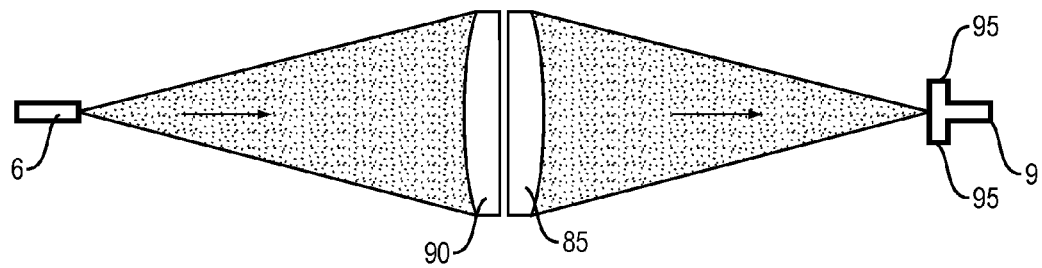

FIGS. 10a, 10b illustrate an embodiment of the device of these teachings with at least two convergent lenses—e.g., a front lens 90 and a back lens 85—and without a lens tube or support tube (which may or may not increase alignment time). Instead, the semiconductor light sources 95 provide multiple wavelength of light that are focused through the positioned lenses 85, 90 and transmitted through the fiber 6, which transmits the coupled light to the target sample and returns the emitted light back through the positioned lenses 85, 90 to the analysis fiber 9. The analysis optical fiber 9 then transmits the emitted light to an attached or integrated analysis component (e.g., a spectrometer).

Figure 11:
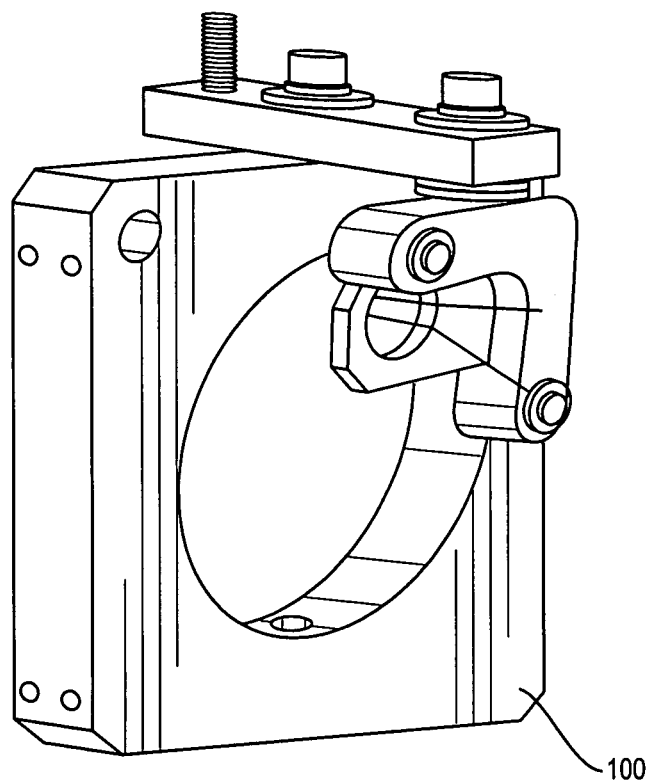
FIG. 11 shows a graphical schematic representation of a component of one embodiment of the system of these teachings.

In embodiments in which the lens tubes are supported by a lens tube support disk 32, such as, but not limited to, the lens tube support disks 32 shown in FIGS. 4B and 4C, fine alignment of the lens tubes is possible in order to improve the coupling between the lens tube assembly 1 and the power fiber 6 (also referred to as the first optical fiber). Fine alignment of the lens tubes is facilitated by an alignment tool 100 that is positioned on the face of the lens tube support disk 32 opposite to the face located opposite to the back lens 2. The alignment tool 100 has fine alignment components that can perform fine displacement, such as fine position of the pointing of the lens tube, of the lens tube to in order to improve its alignment with respect to coupling to the power fiber 6. Once alignment is achieved, the lens tube is secured in place. The lens tube can be secured in place by a number of securing mechanisms, such as, but not limited to, mechanical components and application of epoxy. Application of epoxy would be achieved using an application tool such as, but not limited to, a syringe. The alignment tool 100 is removed away from the lens tube support disk 32 once alignment is achieved. One embodiment of an alignment tool 100 is shown in FIG. 11.

Any suitable hardware and/or software can be used to perform the mechanisms described herein. For example, a general purpose device such as a computer or a special purpose device such as a client, a server, etc. can be used to execute software for performing the mechanisms described herein. Any of these general or special purpose devices can include any suitable components such as a hardware processor (which can be a microprocessor, digital signal processor, a controller, etc.), memory, communication interfaces, display controllers, input devices, etc. This hardware and/or software can be implemented as part of other equipment, such as imaging equipment or analysis equipment, or can be implemented as stand-along equipment (which can be coupled to other equipment).

In some embodiments, any suitable computer readable media can be used for storing instructions for performing the processes described herein. For example, in some embodiments, computer readable media can be transitory or non-transitory. For example, nontransitory computer readable media can include media such as magnetic media (such as hard disks, floppy disks, etc.), optical media (such as compact discs, digital video discs, Blu-ray discs, etc.), semiconductor media (such as flash memory, electrically programmable read only memory (EPROM), electrically erasable programmable read only memory (EEPROM), etc.), any suitable media that is not fleeting or devoid of any semblance of permanence during transmission, and/or any suitable tangible media.

For the purposes of describing and defining the present teachings, it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Although the invention has been described and illustrated in the foregoing illustrative embodiments, it is understood that the present disclosure has been made only by way of example, and that numerous changes in the details of implementation of the invention can be made without departing from the spirit and scope of the invention. Features of the disclosed embodiments can be combined and rearranged in various ways.

What is claimed is:
1. An apparatus comprising:
   a first optical fiber providing optical communication between one surface of the apparatus and a target; the first optical fiber having one end located at said one surface of the apparatus;
   a number of semiconductor light sources, each semiconductor light source from the number of semiconductor light sources disposed on a surface surrounding the first optical fiber and located away from said one end; and
   an optical system optically disposed to receive electromagnetic radiation from said each semiconductor light source and image the electromagnetic radiation received from said each semiconductor light source onto a core area of said one end;

the optical system comprising:
a first lens disposed between said number of semiconductor light sources and said one surface; and
a second lens disposed between said first lens and said one surface; said second lens being optically disposed to receive electromagnetic radiation from said first lens and image the electromagnetic radiation received from said first lens onto a core area of said one end.

2. The apparatus of claim 1 wherein at least some semiconductor light sources from the number of semiconductor light sources emit electromagnetic radiation at a wavelength different from a wavelength of electromagnetic radiation emitted by other semiconductor light sources from the number of semiconductor light sources.

3. The apparatus of claim 1 further comprising:
a second optical fiber providing optical communication between another surface of the apparatus and an analysis component; the second optical fiber having a second optical fiber end located at said another surface of the apparatus; said another surface being disposed away from and facing said one surface; the optical system also being optically disposed to image electromagnetic radiation emanating from said one end of the first optical fiber onto a core area of second optical fiber end.

4. The apparatus of claim 3 wherein
said second lens is optically disposed to receive electromagnetic radiation emanating from said one end of the first optical fiber and said first lens is optically disposed to image electromagnetic radiation received from said second lens onto a core area of second optical fiber end.

5. The apparatus of claim 1 wherein the optical system comprises:
a number of lenses; each one lens from the number of lenses disposed away and receiving electromagnetic radiation from one semiconductor light source from the number of semiconductor light sources; said one lens and said one semiconductor light source constituting a lens/semiconductor light source combination and being one of a number of lens/semiconductor light source combinations; each lens/semiconductor light source combination being located in a lens tube, constituting one of a number of lens tube subsystems.

6. The apparatus of claim 5 wherein each lens tube subsystem is located at an angle with respect to an optical axis defined by a line perpendicular to the core area of the first optical fiber; each lens tube optical axis intersecting the core area of the first optical fiber.

7. The apparatus of claim 5 wherein each lens tube subsystem is located substantially parallel to an optical axis defined by a line perpendicular to the core area of the first optical fiber; said each lens tube subsystem being located at a radial distance away from the optical axis defined by the line perpendicular to the core area of the first optical fiber, the radial distance being larger than a radius of the first optical fiber; said each lens tube subsystem being disposed a distance away from said one surface; and
wherein the optical system is optically disposed to receive electromagnetic radiation from said each lens tube subsystem and image the electromagnetic radiation received from each lens tube subsystem onto a core area of said one end.

8. The apparatus of claim 7 further comprising:
a second optical fiber providing optical communication between another surface of the apparatus and an analysis component; the second optical fiber having a second optical fiber end located at said another surface of the apparatus; said another surface being disposed away from and facing said one surface;
the optical system being also optically disposed to image electromagnetic radiation emanating from one end of the first optical fiber onto a core area of the second optical fiber end.

9. The apparatus of claim 7 wherein
said first lens comprises a number of openings; each opening from said number of openings being optically disposed to receive the electromagnetic radiation from one lens tube subsystem;
said each opening being disposed radially away from an optical axis defined by a line perpendicular to the core area of the first optical fiber; and
said second lens being optically disposed to receive electromagnetic radiation received from said each opening from said number of openings and image the electromagnetic radiation received from said each opening from said number of openings onto a core area of said one end.

10. The apparatus of claim 9 further comprising:
a second optical fiber providing optical communication between another surface of the apparatus and an analysis component; the second optical fiber having a second optical fiber end located at said another surface of the apparatus; said another surface being disposed away from and facing said one surface;
the optical system being also optically disposed to image electromagnetic radiation emanating from said one end of the first optical fiber onto a core area of the second optical fiber end.

11. The apparatus of claim 9 wherein each lens from the number of lenses is a collimating lens.

12. The apparatus of claim 7 further comprising:
a second optical fiber providing optical communication between another surface of the apparatus and analysis component; the second optical fiber having a second optical fiber end located at said another surface of the apparatus; said another surface being disposed away from and facing said one surface.

13. The apparatus of claim 1 wherein each semiconductor light source subsystem is located substantially parallel to an optical axis defined by a line perpendicular to a core area of the first optical fiber; said each semiconductor light source subsystem being located at a radial distance away from the optical axis defined by the line perpendicular to the core area of the first optical fiber, the radical distance being larger than a radius of the first optical fiber; and
at least one semiconductor light source is located substantially radially opposite to another semiconductor light source; said another semiconductor light source being operated as a detector; said another semiconductor light source detecting an output of said at least one semiconductor light source.

14. The apparatus of claim 1 further comprising at least one neutral density filter optically disposed to reduce optical noise.

15. An apparatus comprising:
a first optical fiber providing optical communication between one surface of the apparatus and a target; the first optical fiber having one end located at said one surface of the apparatus;
a number of semiconductor light sources, each semiconductor light source from the number of semiconductor light sources disposed on a surface surrounding the first optical fiber and located away from said one end;

an optical system optically disposed to receive electromagnetic radiation from said each semiconductor light source and image the electromagnetic radiation received from said each semiconductor light source onto a core area of said one end; and a second optical fiber providing optical communication between another surface of the apparatus and an analysis component; the second optical fiber having a second optical fiber end located at said another surface of the apparatus; said another surface being disposed away from and facing said one surface;

the optical system also being optically disposed to image electromagnetic radiation emanating from said one end of the first optical fiber onto a core area of second optical fiber end;

wherein the optical system comprises:

a first lens disposed between said numbers of semiconductor light sources and said one surface; and a second lens disposed between said first lens and said one surface; said second lens being optically disposed to receive electromagnetic radiation from said first lens and image the electromagnetic radiation received from said first lens onto a core area of said one end; said second lens is optically disposed to receive electromagnetically radiation emanating from said one end of the first optical fiber and said first lens is optically disposed to image electromagnetically radiation received from said second lens onto a core area of second optical fiber end;

wherein at least some semiconductor light sources from the number of semiconductor light sources emit electromagnetic radiation at a wavelength different from a wavelength of electromagnetic radiation emitted by other semiconductor light sources from the number of semiconductor light sources.

16. The apparatus of claim 15 wherein the optical system comprises:

a number of lenses; each one lens from the number of lenses disposed away and receiving electromagnetic radiation from one semiconductor light source from the number of semiconductor light sources; said one lens and said one semiconductor light source constituting a lens/semiconductor light source combination and being one of a number of lens/semiconductor light source combinations; each lens/semiconductor light source combination being located in a lens tube, constituting one of a number of lens tube subsystems.

17. The apparatus of claim 16 wherein each lens tube subsystem is located at an angle respect to an optical axis defined by a line perpendicular to the core area of the first optical fiber; each lens tube optical axis intersecting the core area of the first optical fiber.

18. The apparatus of claim 16 wherein each lens tube subsystem is located substantially parallel to an optical axis defined by a line perpendicular to the core area of the first optical fiber; said each lens tube subsystem being located at a radial distance away from the optical axis defined by the line perpendicular to the core area of the first optical fiber, the radial distance being larger than a radius of the first optical fiber; said each lens tube subsystem being disposed a distance away from said one surface; and wherein the optical system optically disposed to receive electromagnetic radiation from said each lens tube subsystem and image the electromagnetic radiation received from each lens tube subsystem onto a core area of said one end.

19. The apparatus of claim 18 wherein said first lens comprises a number of openings; each opening from said number of openings being optically disposed to receive the electromagnetic radiation from one lens tube subsystem; said each opening being disposed radially away from said optical axis; said second lens being optically disposed to receive electromagnetic radiation from said each opening from said number of openings and image the electromagnetic radiation received from said each opening from said number of openings onto a core area of said one end.

20. The apparatus of claim 19 wherein each lens from the number of lenses is a collimating lens.

21. A method for collecting electromagnetic radiation from a target in order to analyze the collected electromagnetic radiation, the method comprising:

coupling first electromagnetic radiation emitted by a number of semiconductor light sources onto a first optical fiber; wherein at least some semiconductor light sources from the number of semiconductor light sources emit electromagnetic radiation at a wavelength different from a wavelength of electromagnetic radiation emitted by other semiconductor light sources from the number of semiconductor light sources;

providing through the first optical fiber, at least a portion of the first electromagnetic radiation emitted by the number of semiconductor light sources to a target;

receiving, through the first optical fiber, second electromagnetic radiation, resulting from providing the at least a portion of the electromagnetic radiation emitted by the number of semiconductor light sources to the target;

coupling at least a portion of the second electromagnetic radiation onto a second optical fiber; and providing, through the second optical fiber, the at least a portion of the second electromagnetic radiation to an analysis component.

22. The method of claim 21 wherein coupling said first electromagnetic radiation emitted by the number of semiconductor light sources comprises:

(a) placing one semiconductor light source in a lens tube;
(b) placing a lens in the lens tube; the lens being disposed away and receiving electromagnetic radiation from the one semiconductor light source;
(c) repeating steps (a) and (b) for each semiconductor light source in the number of semiconductor light sources; thereby forming a number of lens tube subsystems.

23. The method of claim 22 wherein coupling said first electromagnetic radiation emitted by the number of semiconductor light sources further comprises locating each lens tube subsystem at an angle with respect to an optical axis defined by a line perpendicular to a core area of the first optical fiber; each lens tube optical axis intersecting the core area of the first optical fiber.

24. The method of claim 22 wherein coupling said first electromagnetic radiation emitted by the number of semiconductor light sources further comprises:

locating each lens tube subsystem substantially parallel to an optical axis defined by a line perpendicular to a core area of the first optical fiber; said each lens tube subsystem being located at a radial distance away from the optical axis defined by the line perpendicular to the core area of the first optical fiber, the radial distance being larger than a radius of the first optical fiber;

receiving electromagnetic radiation from each lens tube subsystem at an optical subsystem; and imaging, using the optical subsystem, the electromagnetic radiation received from each lens tube subsystem onto a core area of an end of the first optical fiber; wherein the optical subsystem also couples at least a portion of the second electromagnetic radiation onto the first optical fiber.

\* \* \* \* \*